United States Patent
Unverricht et al.

(10) Patent No.: US 6,794,539 B2
(45) Date of Patent: Sep. 21, 2004

(54) METHOD FOR PRODUCING MULTIPLE-PHASE MULTI-METAL OXIDE MATERIALS

(75) Inventors: Signe Unverricht, Mannheim (DE); Raimund Felder, Neustadt (DE); Heiko Arnold, Mannheim (DE); Jochen Petzoldt, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/380,159

(22) PCT Filed: Sep. 20, 2001

(86) PCT No.: PCT/EP01/10910
§ 371 (c)(1),
(2), (4) Date: Mar. 17, 2003

(87) PCT Pub. No.: WO02/24327
PCT Pub. Date: Mar. 28, 2002

(65) Prior Publication Data
US 2003/0181761 A1 Sep. 25, 2003

(30) Foreign Application Priority Data
Sep. 21, 2000 (DE) .......................................... 100 46 928

(51) Int. Cl.$^7$ ....................... C07C 51/16; C07C 51/235; B01J 31/00; B01J 37/00; B01J 23/00
(52) U.S. Cl. ....................... 562/535; 562/531; 562/532; 562/534; 502/104; 502/110; 502/111; 502/113; 502/117; 502/311; 502/312; 502/318; 502/321
(58) Field of Search ................................ 562/531, 532, 562/534, 535; 502/104, 110, 111, 113, 117, 311, 312, 318, 321

(56) References Cited

U.S. PATENT DOCUMENTS

| | | | | |
|---|---|---|---|---|
| 3,898,267 A | * | 8/1975 | Caporali et al. | 558/322 |
| 3,925,464 A | * | 12/1975 | Oda et al. | 562/535 |
| 3,939,208 A | * | 2/1976 | Cavaterra et al. | 568/479 |
| 4,113,769 A | * | 9/1978 | Padovan et al. | 562/534 |
| 4,146,732 A | * | 3/1979 | Padovan et al. | 562/534 |
| 4,166,190 A | * | 8/1979 | White et al. | 562/534 |
| 4,223,161 A | * | 9/1980 | Shaw et al. | 562/534 |
| 4,259,211 A | * | 3/1981 | Krabetz et al. | 502/178 |
| 4,271,040 A | * | 6/1981 | Khoobiar | 502/211 |
| 4,289,654 A | * | 9/1981 | Bertolini et al. | 502/244 |
| 4,298,763 A | * | 11/1981 | Engelbach et al. | 568/479 |
| 4,321,160 A | * | 3/1982 | Farrington et al. | 502/209 |
| 4,365,087 A | * | 12/1982 | Kadowaki et al. | 562/534 |
| 4,438,217 A | * | 3/1984 | Takata et al. | 502/205 |
| 4,471,061 A | * | 9/1984 | Shaw et al. | 502/34 |
| 4,528,398 A | * | 7/1985 | Callahan et al. | 562/534 |
| 4,537,874 A | * | 8/1985 | Sato et al. | 502/311 |
| 4,547,588 A | * | 10/1985 | Khoobiar | 562/535 |
| 4,656,157 A | * | 4/1987 | Hofmann et al. | 502/439 |
| 4,985,592 A | * | 1/1991 | Ishii et al. | 562/534 |
| 5,364,825 A | * | 11/1994 | Neumann et al. | 502/311 |
| 5,449,821 A | * | 9/1995 | Neumann et al. | 562/546 |
| 5,493,052 A | * | 2/1996 | Tenten et al. | 562/534 |
| 5,583,084 A | * | 12/1996 | Martin et al. | 502/211 |
| 5,677,261 A | * | 10/1997 | Tenten et al. | 502/439 |
| 5,807,531 A | * | 9/1998 | Hibst et al. | 252/518.1 |
| 5,910,608 A | * | 6/1999 | Tenten et al. | 562/532 |
| 5,959,143 A | * | 9/1999 | Sugi et al. | 562/534 |
| 6,084,126 A | * | 7/2000 | Hibst et al. | 562/535 |
| 6,124,499 A | * | 9/2000 | Hibst et al. | 562/535 |
| 6,184,173 B1 | * | 2/2001 | Hibst et al. | 502/300 |
| 6,429,332 B1 | * | 8/2002 | Tanimoto et al. | 562/532 |

FOREIGN PATENT DOCUMENTS

| | | |
|---|---|---|
| DE | 198 15 281 | 10/1999 |
| EP | 0 061 830 | 10/1982 |
| EP | 0 756 894 | 2/1997 |

\* cited by examiner

*Primary Examiner*—Cam N. Nguyen
(74) *Attorney, Agent, or Firm*—Oblon, Spivak, McClelland, Maier & Neustadt, P.C.

(57) ABSTRACT

In a process for preparing a multiplephase multimetal oxide composition comprising Mo, V, Cu and, if desired, further elements, at least one phase is preformed separately and dispersed in a plastically deformable precursor composition of a further phase. The mixture is dried and calcined. The multimetal oxide composition is suitable as active composition of catalysts for the catalytically oxidation of organic compounds in the gas phase, in particular for the oxidation of acrolein to acrylic acid.

10 Claims, No Drawings

METHOD FOR PRODUCING MULTIPLE-PHASE MULTI-METAL OXIDE MATERIALS

This application is a 371 of PCT/EP01/10910, filed on Sep. 20, 2001.

The present invention relates to a process for preparing multimetal oxide compositions employed as active composition of catalysts, in particular for the catalytic oxidation of organic compounds in the gas phase, to the multimetal oxide compositions obtainable by means of this process and to a process for preparing acrylic acid using catalysts comprising these multimetal oxide compositions as active composition.

Multimetal oxide compositions containing delineated regions of a promoter phase whose chemical composition is different from its surroundings are known. They are prepared by separately preforming one or more promoter phases in finely divided form and mixing them with sources of the elemental constituents of a host phase. The mixture is then dried if appropriate and calcined. Thus, DE 198 15 281 and EP 0 756 894 state that (a) separately preformed promoter phase(s) can be mixed either dry or wet with the sources of the elemental constituents of the host phase. One possibility is thus to mix the separately preformed promoter phase dry with finely divided starting compounds of the host phase in the desired molar ratio in a mixer, kneader or in a mill. Alternatively, the separately preformed promoter phase can be stirred into an aqueous solution and/or suspension of starting compounds of the host phase and this mixture can subsequently be spray dried.

BACKGROUND OF INVENTION

It has been found that the known production processes are unsatisfactory, in particular for the industrial production of large quantities of catalyst. Thus, the dry mixing of the preformed promoter phase with the starting compounds of the host phase achieves only unsatisfactory mechanical bonding of the phases with one another. On the other hand, stirring the separately preformed promoter phase into an aqueous solution and/or suspension of the elemental constituents of the host phase makes it difficult to achieve a uniform distribution in the host phase because of the high density of the preformed promoter phase. Furthermore, the crystallites of the preformed promoter phase tend to be partly dissolved when stirred into an aqueous solution and/or suspension, particularly when allowed to stand for a prolonged period, as is unavoidable in the processing of large quantities, which blurs the phase boundary and leads to impaired catalyst performance.

SUMMARY OF INVENTION

It is an object of the present invention to provide a process for preparing multimetal oxide compositions comprising a host phase and at least one phase different from the host phase dispersed therein, which process does not have the abovementioned disadvantages. A further object of the invention is to provide a process for preparing multimetal oxide compositions which display improved selectivity in respect of the formation of acrylic acid when used as catalysts for the oxidation of acrolein.

We have found that this object is achieved by a process for preparing multimetal oxide compositions of the formula I $$[A]_p[B]_q[C]_r \quad (I),$$

where A is a phase having the composition $$Mo_{12}V_aX^1_bX^2_cX^3_dX^4_eX^5_fX^6_gO_x,$$

B is a phase having the composition $$X^7_1Cu_hH_iO_y,$$

and C is a phase having the composition $$X^8_1Sb_jH_kO_z,$$

where the variables have the following meanings:
- $X^1$: W, Nb, Ta, Cr and/or Ce, preferably W, Nb and/or Cr,
- $X^2$: Cu, Ni, Co, Fe, Mn and/or Zn, preferably Cu, Ni, Co and/or Fe,
- $X^3$: Sb and/or Bi, preferably Sb,
- $X^4$: Li, Na, K, Rb, Cs and/or H, preferably Na and/or K,
- $X^5$: Mg, Ca, Sr and/or Ba, preferably Ca, Sr and/or Ba,
- $X^6$: Si, Al, Ti and/or Zr, preferably Si, Al and/or Ti,
- $X^7$: Mo, W, V, Nb and/or Ta, preferably Mo and/or W,
- $X^8$: Cu, Ni, Zn, Co, Fe, Cd, Mn, Mg, Ca, Sr and/or Ba, preferably Cu and/or Zn, particularly preferably Cu,
- a: 1 to 8, preferably from 2 to 6,
- b: 0.2 to 5, preferably from 0.5 to 2.5,
- c: 0 to 23, preferably from 0 to 4,
- d: 0 to 50, preferably from 0 to 3,
- e: 0 to 2, preferably from 0 to 0.3,
- f: 0 to 5, preferably from 0 to 2,
- g: 0 to 50, preferably from 0 to 20,
- h: 0.3 to 2.5, preferably from 0.5 to 2, particularly preferably from 0.75 to 1.5,
- i: 0 to 2, preferably from 0 to 1,
- j: 0.05 to 50, preferably from 0.2 to 20, particularly preferably from 0.2 to 5,
- k: 0 to 50, preferably from 0 to 20, particularly preferably from 0 to 12,
- x,y,z: numbers selected so that each phase is electrically neutral, and
- p,q: positive numbers,
- r: 0 or a positive number, where the ratio p/(q+r)=20:1 to 1:20, preferably 5:1 to 1:14, and, when r is a positive number, the ratio q/r=20:1 to 1:20, preferably from 4:1 to 1:4, which comprises i) preforming the phase B and optionally C in finely divided form,
ii) preparing a plastically deformable precursor composition for the phase A, and
iii) dispersing the preformed phase B and optionally C in the precursor composition for the phase A and drying and calcining the composition.

The term "phase" used for the purposes of the present invention refers to three-dimensional regions whose chemical composition is different from their surroundings. The phases are not necessarily X-ray-crystallographically homogeneous. In general, the phase A forms a continuous phase in which the particles of the phase B and optionally C are dispersed.

The finely divided phases B and optionally C advantageously comprise particles whose largest diameter, i.e. the longest line going through the center of gravity of the particle and connecting two points on the surface of the particle, is up to 300 μm, preferably from 0.1 to 200 μm, particularly preferably from 0.5 to 50 μm and very particularly preferably from 1 to 30 μm. However, particles having a largest diameter of from 10 to 80 μm or from 75 to 125 μm are also suitable.

In principle, the phases A, B and C in the multimetal oxide compositions prepared according to the present invention can be amorphous and/or crystalline. It is advantageous for the phase B to consist of crystallites of oxo metalates or comprise oxo metalate crystallites which have the X-ray diffraction pattern and thus the crystal structure type of at least one of the following copper molybdates. The place where the associated X-ray diffraction fingerprint is recorded is given in brackets.

Cu$_4$Mo$_6$O$_{20}$ [A. Moini et al., Inorg. Chem. 25 (21) (1986) 3782–3785],

Cu$_4$Mo$_5$O$_{17}$ [record card 39–181 of the JCPDS-ICDD card index (1991)],

α-CuMoO$_4$ [record card 22–242 of the JCPDS-ICDD card index (1991)],

Cu$_6$Mo$_5$O$_{18}$ [record card 40–865 of the JCPCS-ICDD card index (1991)],

Cu$_{4-x}$Mo$_3$O$_{12}$ where x=0 to 0.25 [record card 24–56 and 26–547 of the JCPCS-ICDD card index (1991)], Cu$_6$Mo$_4$O$_{15}$ [record card 35–17 of the JCPDS-ICDD card index (1991)], Cu$_3$(MoO$_4$)$_2$(OH)$_2$ [record card 36–405 of the JCPDS-ICDD card index (1991)], Cu$_3$Mo$_2$O$_9$ [record card 24–55 and 34–637 of the JCPDS-ICDD card index (1991)], Cu$_2$MoO$_5$ [record card 22–607 of the JCPDS-ICDD card index (1991)].

The phase B preferably comprises oxo metalates which have the X-ray diffraction pattern and thus the crystal structure type of the following copper molybdate:

CuMoO$_4$-III having a wolframite structure as described in Russian Journal of Inorganic Chemistry 36 (7) (1991) 927–928, Table 1.

Among these, preference is given to those having the stoichiometry II below:

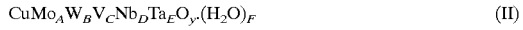

$$CuMo_AW_BV_CNb_DTa_EO_y \cdot (H_2O)_F \qquad (II)$$

where

1/(A+B+C+D+E): 0.7 to 1.3, preferably from 0.85 to 1.15, particularly preferably from 0.95 to 1.05 and very particularly preferably 1, F: 0 to 1, B+C+D+E: 0 to 1, preferably from 0 to 0.7, and y a number determined by the valence and abundance of the elements different from oxygen.

Particular preference is given to compounds of this type which have the stoichiometry III, IV or V:

$$CuMo_AW_BV_CO_y \qquad (III)$$

where

1/(A+B+C): 0.7 to 1.3, preferably from 0.85 to 1.15, particularly preferably from 0.95 to 1.05 and very particularly preferably 1, B+C: 0 to 1, preferably from 0 to 0.7, and y a number determined by the valence and abundance of elements different from oxygen;

$$CuMo_AW_BO_y \qquad (IV)$$

where

1/(A+B): 0.7 to 1.3, preferably from 0.85 to 1.15, particularly preferably from 0.95 to 1.05 and very particularly preferably 1, A, B: 0 to 1 and y a number determined by the valence and abundance of elements different from oxygen;

$$CuMo_AV_CO_y \qquad (V),$$

where

1/(A+C): 0.7 to 1.3, preferably from 0.85 to 1.15, particularly preferably from 0.95 to 1.05 and very particularly preferably 1, A, C: 0 to 1 and y: a number determined by the valence and abundance of elements different from oxygen.

The preparation of such oxo metalates is disclosed, for example, in EP-A 668 104.

Further suitable phases B are ones comprising oxo metalates having the stoichiometry VI below:

$$CuMo_AW_BV_CNb_DTa_EO_y \qquad (VI)$$

where

1/(A+B+C+D+E): 0.7 to 1,3, preferably from 0.85 to 1.15, particularly preferably from 0.95 to 1.05 and very particularly preferably 1, (B+C+D+E)/A: 0.01 to 1, preferably from 0.05 to 0.3, particularly preferably from 0.075 to 0.15 and very particularly preferably 0.11 and y: a number determined by the valence and abundance of elements different from oxygen.

This structure type is referred to as the HT copper molybdate structure and displays an X-ray diffraction pattern (fingerprint) whose most characteristic and most intense diffraction lines, reported as lattice spacings d [Å], are as follows:

6.79±0.3
3.56±0.3
3.54±0.3
3.40±0.3
3.04±0.3
2.96±0.3
2.67±0.2
2.66±0.2
2.56±0.2
2.36±0.2
2.35±0.2
2.27±0.2
2.00±0.2
1.87±0.2
1.70±0.2
1.64±0.2
1.59±0.2
1.57±0.2
1.57±0.2
1.55±0.2
1.51±0.2
1.44±0.2

When the phase B comprises a mixture of various oxo metalates, preference is given to a mixture of oxo metalates having wolframite and HT copper molybdate structures. The weight ratio of crystallites having an HT copper molybdate structure to crystallites having a wolframite structure can be from 0.01 to 100, from 0.1 to 10, from 0.25 to 4 or from 0.5 to 2.

The preparation of oxo metalates VI is disclosed, for example, in DE-A 195 28 646.

The phase C preferably comprises crystallites having the trirutile structure type of α- and/or β-copper antimonate CuSb$_2$O$_6$. α-CuSb$_2$O$_6$ crystallizes in a tetragonal trirutile structure (E.-O. Giere et al., J. Solid State Chem. 131 (1997)

263–274), while β-$CuSb_2O_6$ has a monoclinically distorted trirutile structure (A. Nakua et al., J. Solid State Chem. 91 (1991) 105–112, or reference diffraction pattern on record card 17–284 in the JCPDS-ICDD card index 1989). Preference is also given to phases C which have the pyrochlore structure of the mineral partzite, a copper antimony oxide hydroxide having the variable composition $Cu_ySb_{2-x}(O,OH, H_2O)_{6-7}$ (y×2.0×x×1) (B. Mason et al., Mineral. Mag. 30 (1953) 100–112, or reference pattern on record card 7–303 in the JCPDS-ICDD card index 1996).

The phase C can also comprise crystallites which have the structure of copper antimonate $Cu_9Sb_4O_{19}$ (S. Shimada et al., Chem. Lett. 1983, 1875–1876 or S. Shimada et al., Thermochim. Acta 133 (1988) 73–77, or reference pattern on record card 45–54 of the JCPDS-ICDD card index) and/or the structure of $Cu_4SbO_{4.5}$ (S. Shimada et al., Thermochim. Acta 56 (1982) 73–82 or S. Shimada et al., Thermochim. Acta 133 (1988) 73–77, or reference pattern on record card 36–1106 of the JCPDS-ICDD card index).

Of course, the phase C can also consist of crystallites which represent a mixture of the abovementioned structures.

The preformation of the phase B can be carried out in a simple manner by producing an intimate, preferably finely divided dry mixture of suitable sources of the elemental constituents in the desired stoichiometric ratio and calcining this for a number of hours under inert gas or preferably in air at from 200 to 1000° C., preferably from 250 to 800° C., for a period which could range from a few minutes to a number of hours. The calcination atmosphere may further comprise water vapor. Suitable sources of the elemental constituents of the phase B are oxides and/or compounds which can be converted into oxides by heating, if necessary in the presence of oxygen. Apart from the oxides, suitable starting compounds are, in particular, halides, nitrates, formates, oxalates, citrates, acetates, carbonates, ammine complex salts, ammonium salts and/or hydroxides. Compounds such as $NH_4OH$, $(NH_4)_2CO_3$, $NH_4NO_3$, $NH_4CHO_2$, $CH_3COOH$, $NH_4CH_3CO_2$ or ammonium oxalate which decompose or can be decomposed to compounds which escape completely in gaseous form at the latest during calcination can additionally be incorporated. The intimate mixing of the starting compounds can be carried out dry or wet. If it is carried out dry, the starting compounds are advantageously used as finely divided powders and, after mixing and optionally compaction, are subjected to calcination. However, the intimate mixing is preferably carried out wet. In this method, the starting compounds are usually mixed with one another in the form of an aqueous solution and/or suspension. The aqueous composition obtained is subsequently dried, preferably by spray drying the aqueous mixture at outlet temperatures of, for example, from 100 to 150° C. The dried composition is subsequently calcined.

In another method of preparing the phase B, thermal treatment of the mixture of the starting compounds used is carried out in a pressure vessel (autoclave) at from >100 to 600° C. in the presence of steam at superatmospheric pressure. The pressure range typically extends up to 500 atm, preferably up to 250 atm. This hydrothermal treatment is particularly advantageously carried out in a temperature range from >100 to 374.15° C. (critical temperature of water) in which water vapor and liquid water coexist under the pressures established.

The multimetal oxide compositions obtained as described, which may comprise oxo metalates of a single structure type or a mixture of oxo metalates of various structure types, are, optionally after milling and/or classification to the desired size, used as finely divided phase B.

The phase C can be prepared in the same way as described above for the phase B.

Preference is given to preparing a dry mixture of the elemental constituents of the phase C in which at least part, preferably all, of the antimony is present in the oxidation state +5 and calcining this at from 200 to 1200° C., preferably from 200 to 850° C., particularly preferably from 300 to 850° C., under inert gas or preferably in air. The calcination atmosphere may further comprise water vapor. Multimetal oxide compositions suitable as phase C are obtainable, for example, by the methods described comprehensively in DE-A 24 07 677. Among these, preference is given to oxidizing antimony trioxide or $Sb_2O_4$ in aqueous medium by means of hydrogen peroxide in an amount below, equal to or above the stoichiometric amount at from 40 to 100° C. to form antimony (V) oxide hydroxide, adding aqueous solutions and/or suspensions of suitable starting compounds of the other elemental constituents of phase C before, during and/or after this oxidation, subsequently drying the resulting aqueous mixture (preferably spray drying it, inlet temperature: 200 to 600° C., outlet temperature: 80 to 130° C.) and then calcining the intimate dry mixture as described.

In the process just described, it is possible to use, for example, aqueous hydrogen peroxide solutions having an $H_2O_2$ content of from 5 to 33% by weight. Addition of suitable starting compounds of the other elemental constituents of the phase C after the $H_2O_2$ oxidation is particularly advisable when these are able to decompose the hydrogen peroxide catalytically. Of course, it is also possible to isolate the antimony (V) oxide hydroxide from the aqueous medium and, for example, to mix it intimately with suitable finely divided starting compounds of the other elemental constituents of phase C and, if desired, further Sb starting compounds and subsequently calcine this intimate mixture as described.

It is important that the element sources of the phase C are either oxides or compounds which can be converted into oxides by heating, if necessary in the presence of oxygen. Apart from the oxides, suitable starting compounds are therefore, in particular, halides, nitrates, formates, oxalates, acetates, carbonates and/or hydroxides. Compounds such as $NH_4OH$, $(NH_4)_2CO_3$, $NH_4NO_3$, $NH_4CHO_2$, $CH_3COOH$, $NH_4CH_3CO_2$ or ammonium oxalate which decompose or can be decomposed to compounds which escape in gaseous form at the latest during calcination can additionally be incorporated.

In general, the intimate mixing of the starting compounds to produce the phase C can also be carried out dry or wet. If it is carried out dry, the starting compounds are advantageously used as finely divided powders. However, the intimate mixing is preferably carried out wet. In this method, the starting compounds are usually mixed with one another in the form of an aqueous solution and/or suspension. After mixing has been concluded, the fluid mass is dried and then calcined. Here too, drying is preferably carried out by spray drying. After calcination, the oxo metalates obtained can be comminuted, for example by wet or dry milling, e.g. in a ball mill or by jet milling. The particle size fraction having the range of largest diameters desired for the phase C can be separated off from the resulting powder, which generally consists of essentially spherical particles. A preferred method of preparing a phase C of the formula $(Cu,Zn)_1Sb_hH_xO_y$ comprises firstly converting antimony trioxide and/or $Sb_2O_4$ in an aqueous medium into a preferably finely divided Sb(V) compound, e.g. antimony(V) oxide hydroxide hydrate, by means of hydrogen peroxide, admixing the resulting aqueous suspension with an ammoniacal aqueous solution of zinc carbonate and/or copper carbonate (which may have, for example, the composition $Cu_2(OH)_2CO_3$), drying the resulting aqueous mixture, e.g. by spray drying, and calcining the resulting powder as described. Between the drying and calcination steps, the powder may, if desired, be compounded with water and subsequently extruded and the extrudates dried.

The plastically deformable precursor composition for the phase A comprises sources of the elemental constituents of the phase A. Suitable sources are likewise oxides and/or compounds which can be converted into oxides by heating, if necessary in the presence of oxygen. Apart from oxides, suitable starting compounds of this type are, in particular, halides, nitrates, formates, oxalates, citrates, acetates, carbonates and/or hydroxides. Compounds such as $NH_4OH$, $(NH_4)_2CO_3$, $NH_4HCO_3$, $NH_4NO_3$, $NH_4CHO_2$, $CH_3COOH$ or $NH_4CH_3CO_2$, which decompose or can be decomposed to form compounds which escape completely in gaseous form at the latest during calcination can additionally be incorporated. Particularly suitable starting compounds of Mo, V, W and Nb also include their oxo compounds, i.e. molybdates, vanadates, tungstates and niobates, in particular the corresponding ammonium compounds such as ammonium molybdate, ammonium vanadate, ammonium tungstate, and the corresponding acids.

The terms "plastically deformable" and "paste-like" refer to a consistency which is coherent (and is not, as in the case of a powder, made up of discrete particles) and is deformable only under the action of a certain force (and does not, as in the case of a solution or suspension, spontaneously assume the shape of a vessel). The yield point of the plastically deformable precursor composition, i.e. the smallest shear stress measured in pascal [Pa] above which it behaves rheologically like a liquid, is preferably in the range from about 1 to 300 KPa, preferably from 10 to 100 KPa.

To produce the plastically deformable precursor composition for the phase A, water can be withdrawn in a controlled manner from an aqueous solution or suspension of the elemental constituents of the phase A until a paste-like residue is obtained. However, in most cases it is more practical to plasticize a dry mixture comprising the sources of the elemental constituents of the phase A in the desired stoichiometric ratio by means of a small amount of a solvent, e.g. from 5 to 100 parts by weight, preferably from 10 to 30 parts by weight, of solvent per 100 parts by weight of dry mixture. To carry out the plasticization, it is possible to use all apparatuses known to those skilled in the art for the homogenization of highly viscous compositions, in particular kneaders which can operate in a batch mode or continuously. Alternatively, use can also be made of fast-running mechanical mixers such as blade mixers, ribbon mixers or inclined mixers, which may be equipped with high-speed cutters. It is also possible to use Eirich countercurrent mixers or pan mixers. Finally, annular trough mixers can also be used if they are equipped with edge runners and high-speed swirlers.

The dry mixture can be produced by dry mixing of the starting compounds, preferably in the form of finely divided powders. However, the dry mixture is preferably obtained by mixing the starting compounds with one another so as to form an aqueous solution and/or suspension. The solution and/or suspension is subsequently dried, preferably by spray drying, with outlet temperatures of from 100 to 150° C. being suitable.

Suitable solvents are all solvents which vaporize without leaving a significant residue or decompose without leaving a significant residue during calcination at up to about 360° C. The solvent is advantageously chosen so that it readily wets the dry mixture. Examples of suitable solvents are water, carboxylic acids, which may be branched or straight-chain, saturated or unsaturated, e.g. formic acid, acetic acid, primary or secondary $C_1$–$C_8$-alcohols such as methanol, ethanol, 2-propanol, aldehydes, ketones such as acetone, and mixtures thereof. The solvent vapor and/or decomposition gases of the solvent which escape during drying and/or calcination contribute to a favorable pore structure in the multimetal oxide compositions.

Kneaders which can be used are, for example, continuous screw kneaders or trough kneaders. Continuous screw kneaders have one or more screws which are located in a cylindrical barrel parallel to its axis and comprise a shaft and, attached thereto, kneading and transport elements which convey the material introduced at one end of the kneader to the outlet end of the kneader and at the same time plasticize and homogenize it. Trough kneaders having at least two horizontally mounted rotors, e.g. a double-blade trough kneader with two contrarotating kneading blades in a double cavity trough, have been found to be particularly useful. The rotors can have different shapes, e.g. sigma shape, masticator shape, hub shape, etc.

The preformed phase B and optionally C is/are then dispersed in the plastically deformable precursor composition for the phase A. To disperse or finely distribute the preformed phase B and optionally C in the plastically deformable precursor composition for the phase A, it is advantageous to use the abovementioned apparatuses, e.g. kneaders. If, as in a preferred embodiment of the invention, the plastically deformable precursor composition for the phase A is obtained by plasticization of a dry mixture by means of a small amount of solvent in an apparatus suitable for this purpose, plasticization and subsequent dispersion of the preformed phase B and optionally C advantageously take place in the same apparatus.

It is advantageous for the incorporation of the preformed phase B and optionally C into the plastically deformable precursor composition for the phase A to be carried out at at below 90° C., preferably below 80° C. and particularly preferably below 60° C. The incorporation temperature is generally more than 0° C. and mostly from 20° C. to 45° C.

Furthermore, it is advantageous for the time from dispersion of the preformed phase B and optionally C in the precursor composition for the phase A to drying of the composition to be less than 24 hours, preferably less than 12 hours, in particular less than 6 hours.

The composition obtained after dispersion of the preformed phase B and optionally C in the precursor composition for the phase A is advantageously shaped to give shaped bodies. The use of an extruder is particularly appropriate for this purpose. The product of extrusion is advantageously extrudates having a diameter of, for example, from 3 to 20 mm and a length of, for example, from 0.5 to 4 cm.

The shaped or unshaped precursor compositions are dried at, in general, from 50 to 180° C., e.g. about 120° C., prior to calcination.

The calcination of the precursor compositions to produce the actual catalytically active multimetal oxide compositions is generally carried out, regardless of whether it is before or after shaping, at from 250 to 600° C., preferably from 300 to 450° C. Calcination can be carried out under inert gas, e.g. nitrogen, a mixture of inert gas and oxygen, e.g. air, reducing gases such as hydrocarbons, e.g. methane, aldehydes, e.g. acrolein, or ammonia, or else under a mixture of $O_2$ and reducing gases, as described, for example, in DE-A 4335973. When calcination is carried out under reducing conditions, care has to be taken to ensure that the metallic constituents are not reduced to the element. The calcination is therefore advantageously carried out under an oxidizing atmosphere. The calcination time is generally a number of hours and decreases in the usual fashion as the calcination temperature increases. Various types of furnace, e.g. tray furnaces, rotary tube furnaces, belt calciners, fluidized-bed furnaces or shaft furnaces, are possible for carrying out the calcination.

For use as catalyst, the multimetal oxide compositions of the formula I are generally shaped to obtain a desired catalyst geometry, preferably by application to preshaped inert catalyst supports, with the application to the support being able to be carried out before or after the final calcination. In general, the relevant composition is calcined before application to the support. Coating of the support bodies to produce coated catalysts is generally carried out in a suitable rotatable vessel as is known, for example, from DE-A 29 09 671 or from EP-A 293 859. To coat the support bodies, the powder composition to be applied is advantageously moistened and dried again after application, e.g. by means of hot air. The thickness of the layer of powder composition-applied to the support body is advantageously in the range from 50 to 500 μm, preferably in the range from 150 to 250 μm.

The powder composition can also advantageously be applied to the support bodies from a suspension, e.g. by spraying the dispersion onto the agitated support bodies while simultaneously passing an inert gas over the bodies, as described in EP-A 15569.

Support materials which can be used are customary porous or nonporous aluminum oxides, silicon dioxide, thorium dioxide, zirconium dioxide, silicon carbide or silicates such as magnesium silicate or aluminum silicate. The support bodies can have regular or irregular shapes, with regularly shaped support bodies having a distinct surface roughness, e.g. spheres or hollow cylinders, being preferred. It is particularly advantageous to use essentially nonporous steatite rings having a rough surface and an external diameter of from 4 to 10 mm (cf. DE-A 4442346).

Alternatively, the multimetal oxide composition obtainable according to the present invention can also be used for producing all-active catalysts. For this purpose, the precursor composition is, before or after calcination, compacted to produce the desired catalyst geometry (e.g. by tableting, extrusion or ram extrusion), if appropriate with addition of customary auxiliaries such as graphite or stearic acid as lubricants and/or shaping aids and reinforcing materials such as microfibers of glass, asbestos, silicon carbide or potassium titanate. Preferred all-active catalyst geometries are hollow cylinders having an external diameter and a length of from 2 to 10 mm and a wall thickness of from 1 to 3 mm.

The multimetal oxide compositions obtainable according to the present invention are particularly suitable as catalysts having increased selectivity (at a given conversion) for the gas-phase catalytic of acrolein to acrylic acid. The process is normally carried out using acrolein which has been produced by catalytic gas-phase oxidation of propene. In general, the acrolein-containing reaction gases from this propene oxidation are used without intermediate purification. The gas-phase catalytic oxidation of acrolein is usually carried out as a heterogeneous fixed-bed oxidation in shell-and-tube reactors. As oxidant, oxygen is used in a manner known per se, advantageously diluted with inert gases (e.g. in the form of air). Suitable diluent gases are, for example, $N_2$, $CO_2$, hydrocarbons, recirculated offgases from the reaction and/or steam. The acrolein oxidation is generally carried out using an acrolein:oxygen:water vapor:inert gas volume ratio of 1:(1–3):(0–20):(3–30), preferably 1:(1–3):(0.5–10):(7–18). The reaction pressure is generally from 1 to 3 bar and the total space velocity is preferably from 1000 to 4500 standard l/(l·h). Typical multitube fixed-bed reactors are described, for example, in DE-A 28 30 765, DE-A 22 01 528 or U.S. Pat. No. 3,147,084. The reaction temperature is customarily selected so that the acrolein conversion on a single pass is above 90%, preferably above 98%. This normally requires reaction temperatures of from 230 to 330° C.

Apart from the gas-phase catalytic oxidation of acrolein to acrylic acid, the process products of the present invention are also able to catalyze the gas-phase oxidation of other organic compounds, in particular other alkanes, alkanols, alkanals, alkenes and alkenols preferably having from 3 to 6 carbon atoms (e.g. propylene, methacrolein, tert-butanol, the methyl ether of tert-butanol, isobutene, isobutane or isobutyraldehyde) to give olefinically unsaturated aldehydes and/or carboxylic acids, and also the corresponding nitriles (ammoxidation, especially of propene to acrylonitrile and of isobutene or tert-butanol to methacrylonitrile). Examples which may be mentioned are the preparation of acrolein, methacrolein and methacrylic acid. However, they are also useful for the oxidative dehydrogenation of olefinic compounds.

In the present text, conversion, selectivity and residence time are, unless indicated otherwise, defined as follows:

$$\text{Conversion } C \text{ of acrolein (\%)} = \frac{\text{Number of mol of acrolein reacted}}{\text{Number of mol of acrolein fed in}} \times 100$$

$$\text{Selectivity } S \text{ of acrylic acid formation} = \frac{\text{Number of mol converted into acrylic acid}}{\text{Number of mol of acrolein reacted}} \times 100$$

$$\text{Residence time (sec)} = \frac{\text{Empty volume of reactor filled with catalyst (l)}}{\text{Flow rate of synthesis gas (standard l/h)}} \times 3\,600$$

EXAMPLE

Preparative Example 1 a) Preformation of the Phase B having the Stoichiometry $Cu_{1.0}Mo_{0.5}W_{0.5}O_4$ A first stirred vessel was charged with 620 l of water at about 25° C. while stirring. 27.4 kg of $(NH_4)_6Mo_7O_{24}*4H_2O$ were subsequently added thereto. After heating, 40.4 kg of $(NH_4)_{10}W_{12}O_{41}*7H_2O$ were added and the mixture was heated to 90° C. while continuing to stir. A clear, yellow-orange solution was obtained (solution 1).

In parallel to the preparation of solution 1, a second stirred vessel was charged with 373 l of water at about 25° C. while stirring. 61 l of 25% strength by weight aqueous $NH_3$ solution were subsequently stirred in. 61.9 kg of copper(II) acetate were added to the ammoniacal solution and the resulting mixture was stirred until a clear, dark blue solution without sediment was obtained (solution 2).

Solution 2 was transferred from the second stirred vessel into solution 1. The turquoise slurry obtained was subsequently spray dried at a gas inlet temperature into the spray dryer of 250° C. and a gas outlet temperature of 140° C. Spray drying was carried out in cocurrent.

75 kg of the spray-dried powder were introduced into a kneader and kneaded with addition of 15 l of water. The kneaded material was then emptied into an extruder and shaped by means of the extruder to form extrudates (length: 1–2 cm; diameter: 6 mm).

The extrudates were dried at 120° C. on a belt dryer.

The catalyst precursor was calcined continuously in a rotary tube at 340° C. and a residence time of at least 1 h in a stream of air. The precursor was subsequently calcined again at 790° C.

The extrudates were subsequently milled in a Biplex BQ 500 mill to a mean particle diameter of 3–5 μm.

The resulting ground material had a BET surface area of ×1 m²/g. X-ray diffraction identified the following phases:

1. $CuMoO_4$-III having the wolframite structure,

2. HT copper molybdate.

b) Preformation of the Precursor Composition for the Phase A having the Stoichiometry $Mo_{10.4}V_3W_{1.2}O_x$ A stirred vessel was charged with 900 l of water at about 25° C. while stirring (70 rpm). 122.4 kg of $(NH_4)_6Mo_7O_{24}*H_2O$ were subsequently added thereto and the mixture was heated to 90° C. while stirring. 22.2 kg of NH$_4$VO$_3$ (ammonium metavanadate) were subsequently added. 20.9 kg of (NH$_4$)$_{10}$W$_{12}$O$_{41}$*7H$_2$O were then added; stirring for 60 minutes at 90° C. gave a clear orange solution. Its pH was 6.2 0.3. The pH was firstly reduced to 5.0 0.3 by addition of acetic acid and subsequently increased again to 6.2 0.3 by stirring in 25% strength by weight aqueous NH$_3$ solution. The result was a clear, orange solution without sediment. This was subsequently spray dried at a gas inlet temperature into the spray dryer of 240° C. and a gas outlet temperature of 100° C. The spray-dried powder was a light-yellow color.

c) Preparation of the Active Multimetal Oxide Composition 75 kg of the spray-dried powder obtained in b) were placed in a trough kneader provided with two Z-shaped, horizontally mounted kneading blades. 8.6 l of acetic acid were then added and a kneadable consistency was subsequently produced by addition of the necessary amount of water. 12.9 kg of the phase B which had been prepared beforehand were subsequently added and kneaded until the mass was homogeneous. The kneaded material was then emptied into an extruder and shaped by means of the extruder to produce extrudates (length: 1–2 cm; diameter: 6 mm). The extrudates were dried at 120° C. on a belt dryer.

300 kg of the shaped bodies produced in this way were loaded on a tray cart equipped with 10 trays each having a length of 1 m and a width of 50 cm. The trays were arranged in two rows next to and equidistant from one another. The trays were made of perforated metal sheet having a hole diameter of 3 mm. The tray cart was pushed into a tray furnace (interior dimensions: height×width×length: 1.30 m×1.18 m×1.10 m) which was operated in a convection mode with an gas circulation of about 2500 m$^3$/h. The process gas was electrically heated, and temperature regulation was via a thermocouple in the gas stream. The product temperature was monitored by means of 20 thermocouples which were installed approximately in the middle of the trays in the middle of the product bed. In this furnace, the shaped bodies were calcined in a gas atmosphere made up of 1.5% by volume of O$_2$, 7% by volume of NH$_3$, balance N$_2$, as follows:

The temperature of the gas mixture flowing through the tray furnace was increased in appropriate heating zones of the tray furnace at a rate of 5° C. per minute from room temperature to 325° C. and held at this value for 11 hours. The NH$_3$ content of the gas atmosphere was subsequently reduced to 0%. The temperature was then increased at a rate of 2.5° C./min to 400° C. and this temperature was maintained for 80 minutes. The furnace was subsequently cooled to room temperature.

The calcined extrudates obtained in this way were milled in a Biplex BQ 500 mill to give two-phase, active multimetal oxide composition powder having a mean particle diameter of 3–5 μm.

d) Catalyst Production 70 kg of steatite rings (external diameter×height×internal diameter=7 mm×3 mm×4 mm) as catalyst supports were placed in a coating drum and coated as follows with active multimetal oxide composition powder:

By means of a metering chute, a total of 18.1 kg of active multimetal oxide composition powder were introduced into the coating drum. In parallel thereto, a total amount of 3.5 l of a glycerol/water mixture (weight ratio of glycerol:water=3:1) were metered in as adhesion liquid.

Finally, the coated rings were dried in the coating drum. The proportion of active composition in the coated catalysts produced in this way was about 20% of their weight.

Preparative Example 2

Preparative example 1 was repeated, but a precursor composition for the phase A having the stoichiometry Mo$_{10.4}$V$_4$W$_{1.2}$O$_x$ was prepared in step b) by using 29.6 kg of ammonium metavanadate.

Preparative Example 3

Preparative example 1 was repeated, but only 10.3 kg of the preformed phase B were used in step c).

Example 1

Gas-Phase Catalytic Fixed-Bed Oxidation

For the gas-phase fixed-bed oxidation of acrolein to acrylic acid, the catalyst tubes of a shell-and-tube reactor were charged with the catalyst from preparative example 1 as a fixed bed. Looking in the flow direction of the reaction gas mixture, the tubes were charged firstly with a mixture of uncoated steatite rings (30% by volume) and ring catalysts (70% by volume) and subsequently with only ring catalysts.

The composition of the gas mixture introduced was approximately:

5.5% by volume of acrolein,
0.3% by volume of propene,
0.55% by volume of CO,
1.0% by volume of CO$_2$,
0.3% by volume of acrylic acid,
7.0% by volume of H$_2$O,
6.0% by volume of oxygen, and nitrogen as balance.

Conversion C and selectivity S of acrylic acid formation were as follows:

Throughput: 87 standard l of acrolein/l$_{cat}$·h

C=99.5%, S$_{ACA}$=96%, T=260° C.

Example 2

Example 1 was repeated, but the throughput was 130 standard l of acrolein/l$_{cat}$·h. Conversion C and selectivity S of acrylic acid formation were as follows:

C=99.5%, S$_{ACA}$=96%, T=267° C.

Example 3

Example 1 was repeated, but the catalyst from preparative example 2 was used. Conversion C and selectivity S of acrylic acid formation were as follows:

C=99.5%, S$_{ACA}$=95.8%, T=262° C.

Example 4

Example 3 was repeated, but the throughput was 130 standard l of acrolein/l$_{cat}$·h. Conversion C and selectivity S of acrylic acid formation were as follows:

C=99.4%, S$_{ACA}$=95.9%, T=271° C.

Example 5

Example 1 was repeated, but the catalyst from preparative example 3 was used. Conversion C and selectivity S of acrylic acid formation were as follows:

C=99.5%, S$_{ACA}$=95.9%, T=255° C.

Example 6

Example 5 was repeated, but the throughput was 130 standard 1 of acrolein/$l_{cat}$·h. Conversion C and selectivity S of acrylic acid formation were as follows:

C=99.5%, $S_{ACA}$=95.9%, T=264° C.

Comparative Examples

Preparative Example 4 (Comparison)

The preformation of the phase B having the stoichiometry $Cu_{1.0}Mo_{0.5}W_{0.5}O_4$ was carried out as described in preparative example 1, step a).

A stirred vessel was charged with 850 l of water at about 25° C. 111 kg of $(NH_4)_6Mo_7O_{24}*4H_2O$ were subsequently added thereto and the mixture was heated to 90° C. while stirring. 22 kg of $NH_4VO_3$ were subsequently added, followed after stirring for 20 minutes by 10 kg of $(NH_4)_{10}W_{12}O_{41}*7H_2O$; stirring for 60 minutes at 90° C. gave a clear orange solution having a pH of 5.5–6. The pH was reduced to 4–5 by addition of acetic acid and subsequently increased again to 5.5–6 by stirring in 25% strength by weight aqueous $NH_3$ solution. 26 kg of the previously prepared phase B were added to this solution and the mixture was stirred for another 30 minutes. The slurry obtained was spray dried.

The further production of the catalyst was carried out as described in preparative example 1, steps c) and d), with no phase B being added in step c).

Preparative Example 5 (Comparison)

275 l of water were placed in a stirred vessel and 16.3 kg of copper acetate were dissolved therein while stirring. This gave a clear solution (solution 1).

Separately therefrom, 615 l of water were placed in a stirred vessel and 73.0 kg of ammonium heptamolybdate were dissolved therein, the resulting solution was heated to 90° C. and 12.0 kg of ammonium metavanadate and subsequently 10.2 kg of $(NH_4)_{10}W_{12}O_{41}*7H_2O$ were added (solution 2).

Solution 1 was subsequently drained into solution 2 while stirring and the mixture obtained was admixed with 25% strength by weight aqueous $NH_3$ solution until the pH was 8.5. The slurry obtained was spray dried at a gas inlet temperature on the spray dryer of 240° C. and a gas outlet temperature of 100° C.

The further production of the catalyst was carried out as described in preparative example 1, steps c) and d), but with no phase B being added in step c).

Comparative Example 7

Example 1 was repeated, but the catalyst from preparative example 4 was used. Conversion C and selectivity S of acrylic acid formation were as follows:

C=99.5%, $S_{ACA}$=94.5%, T=248° C.

Comparative Example 8

Comparative example 7 was repeated, but the throughput was 130 standard 1 of acrolein/$l_{cat}$·h. Conversion C and selectivity S of acrylic acid formation were as follows:

C=99.5%, $S_{ACA}$=94.7%, T=257° C.

Comparative Example 9

Example 1 was repeated, but the catalyst from preparative example 5 was used. Conversion C and selectivity S of acrylic acid formation were as follows:

C=99.5%, $S_{ACA}$=95.0%, T=260° C.

Comparative Example 10

Example 9 was repeated, but the throughput was 130 standard 1 of acrolein/$l_{cat}$·h. Conversion C and selectivity S of acrylic acid formation were as follows:

C=99.5%, $S_{ACA}$=95.0%, T=266° C.

We claim:

1. A process for preparing multimetal oxide compositions of the formula I $$[A]_p[B]_q[C]_r \quad (I),$$

where A is a phase having the composition $$Mo_{12}V_aX^1_bX^2_cX^3_dX^4_eX^5_fX^6_gO_x,$$

B is a phase having the composition $$X^7_1Cu_hH_iO_y$$

and C is a phase having the composition $$X^8_1Sb_jH_kO_z$$

wherein
- $X^1$: W, Nb, and/or Cr,
- $X^2$: Cu, Ni, Co, and/or Fe,
- $X^3$: Sb,
- $X^4$: Na and/or K,
- $X^5$: Ca, Sr, and/or Ba,
- $X^6$: Si, Al, and/or Ti,
- $X^7$: Mo and/or W,
- $X^8$: Cu and/or Zn,
- a: 2 to 6,
- b: 0.5 to 2.5,
- c: 0 to 4,
- d: 0 to 3,
- e: 0 to 0.3,
- f: 0 to 2,
- g: 0 to 20,
- h: 0.5 to 2,
- i: 0 to 1,
- j: 0.2 to 20,
- k: 0 to 20,
- x,y,z: numbers selected so that each phase is electrically neutral, and
- p,q: positive numbers,
- r: 0 or a positive number, where the ratio p/(q+r)=20:1 to 1:20 and, when r is a positive number, the ratio q/r=20:1 to 1:20, said process comprises
- i) preforming the phase B and optionally C in finely divided form,
- ii) preparing a plastically deformable precursor composition for the phase A, and
- iii) dispersing the preformed phase B and optionally C in the precursor composition for the phase A and drying and calcining the composition.

2. A process as claimed in claim 1, wherein the plastically deformable precursor composition for the phase A is obtained by plasticizing a dry mixture comprising sources of the elemental constituents of the phase A and by solvent in the amount of from 5 to 100 parts by weight of a solvent per 100 parts by weight of powder.

3. A process as claimed in claim 2, wherein the solvent is selected from among water, carboxylic acids, primary and secondary $C_1$–$C_8$-alcohols, aldehydes, ketones and mixtures thereof.

4. A process as claimed in claim 2, wherein the dry mixture is plasticized in a trough kneader having at least two horizontally mounted rotors and the preformed phase B and optionally C is/are dispersed in the precursor composition for the phase A in the same kneader.

5. A process as claimed in claim 1, wherein dispersion of the preformed phase B and optionally C in the precursor composition for the phase A is carried out at 90° C. or below.

6. A process as claimed in claim 1, wherein the time from dispersion of the preformed phase B and optionally C in the precursor composition for the phase A to drying of the composition is less than 24 hours.

7. A process as claimed in claim 6, wherein the time from dispersion of the preformed phase B and optionally C in the precursor composition for the phase A to drying of the composition is less than 12 hours.

8. A multimetal oxide composition prepared by a process as claimed in claim 1.

9. A catalyst comprising a multimetal oxide composition as claimed in claim 8 as active composition.

10. A process for preparing acrylic acid by gas-phase catalytic oxidation of acrolein, in the presence of a catalyst as claimed in claim 9.

* * * * *